US00PP22169P2

(12) United States Plant Patent
Saul

(10) Patent No.: US PP22,169 P2
(45) Date of Patent: Sep. 27, 2011

(54) ×*HEUCHERELLA* PLANT NAMED 'BLUE RIDGE'

(50) Latin Name: ×*Heucherella*
Varietal Denomination: Blue Ridge

(75) Inventor: Richard G. Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 0 days.

(21) Appl. No.: 12/807,529

(22) Filed: Sep. 8, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — Kent L Bell
(74) *Attorney, Agent, or Firm* — Penny J. Aguirre

(57) ABSTRACT

A new cultivar of ×*Heucherella,* 'Blue Ridge', characterized by its foliage that is silver-green in color with burgundy veins with a thin green margin on the upper surface and green in color on the lower surface, its large ovate-shaped leaves that average 8 cm in length, its clean white flowers in early spring, and its tolerance to heat, humidity, and exposure to sunlight with good garden performance in the southern regions of the U.S.

2 Drawing Sheets

Botanical classification: ×*Heucherella.*
Cultivar designation: 'Blue Ridge'.

CROSS REFERENCE TO A RELATED APPLICATION

This application is co-pending with a U.S. Plant Patent Application filed for a plant derived from the same cross in the Inventor's breeding program that is entitled *Heucherella* Plant Named 'Cumberland' (U.S. Plant patent application Ser. No. 12/807,553).

BACKGROUND OF THE INVENTION

The present invention relates to a new and distinct cultivar of ×*Heucherella,* and is hereinafter referred to by the cultivar name 'Blue Ridge'.

The new cultivar was derived from a controlled breeding program conducted by the Inventor in Dahlonega, Ga. with the objective of creating new cultivars of ×*Heucherella* that are heat tolerant and suitable for use in southern regions of the United States. The Inventor made a cross in March of 2008 between an unnamed plant of *Tiarella cordifolia* as the female parent and *Heuchera*×*villosa* 'Pinor Noir' (U.S. Plant Pat. No. 20,434) as the male parent. The Inventor selected 'Blue Ridge' in April of 2009 as a single unique plant amongst the seedlings that resulted from the above cross.

Asexual reproduction of the new cultivar was first accomplished under direction of the Inventor by in vitro propagation in Alpharetta, Ga. in April of 2009. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Blue Ridge' as a new and unique cultivar of ×*Heucherella.*

1. 'Blue Ridge' exhibits foliage that is silver-green in color with burgundy veins with a thin green margin on the upper surface and green in color on the lower surface.

2. 'Blue Ridge' exhibits large ovate-shaped leaves that average 8 cm in length when mature.
3. 'Blue Ridge' obtains a height of 15 cm with blooms reaching 30 cm in height.
4. 'Blue Ridge' exhibits clean white flowers in early spring that are more typical of *Tiarella* than *Heuchera.*
5. 'Blue Ridge' exhibits tolerance to heat and humidity, and has performed well in the southern regions of the U.S.

'Blue Ridge' can be compared to its parent plants an unnamed plant of, *Tiarella cordifolia* and *Heuchera* 'Pinot Noir'. The unnamed plant of *Tiarella cordifolia* differs from 'Blue Ridge' in having green foliage with white flowers that bloom earlier in the spring. 'Pinot Noir' differs from 'Blue Ridge' in having flowers that are white in color and tinged with burgundy, reach 46 cm in height and blooming in late spring and in having foliage that reaches 25 cm in height and is burgundy in color with a silver overlay and burgundy veins. 'Blue Ridge' can be most closely compared to the ×*Heucherella* cultivar 'Heart of Darkness' (U.S. Plant Pat. No. 14,489). 'Heart of Darkness' is similar to 'Blue Ridge' in having silver foliage with burgundy veins and in having white flowers. 'Heart of Darkness' differs from 'Blue Ridge' in having leaves that are burgundy in color on the lower surface, flower scapes that are taller in height (60 cm) and in being less hardy for southern gardeners as *Heuchera*×*villosa* is not in its heritage.

BRIEF DESCRIPTION OF THE DRAWING

The accompanying colored photographs illustrate the overall appearance and distinct characteristics of the new ×*Heucherella.* The photographs were taken of a two year-old plant of 'Blue Ridge' as grown outdoors in a 2-gallon container in Georgia.

The photograph on FIG. 1 provides a view of the habit and foliage coloration of 'Blue Ridge' in bloom and The photograph in FIG. 2 provides a close-up view of the foliage of 'Blue Ridge'.

Figure 1:
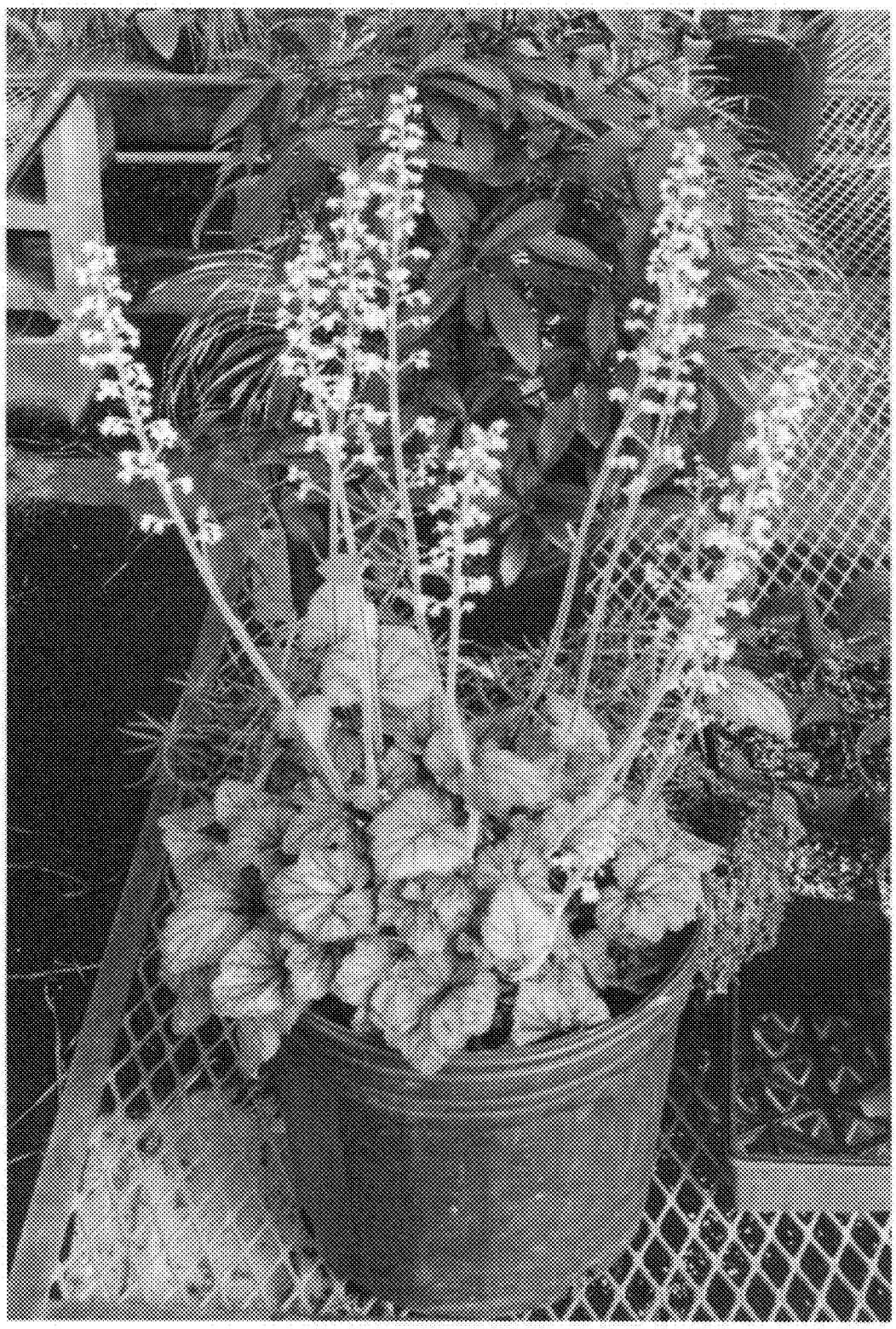
Figure 2:
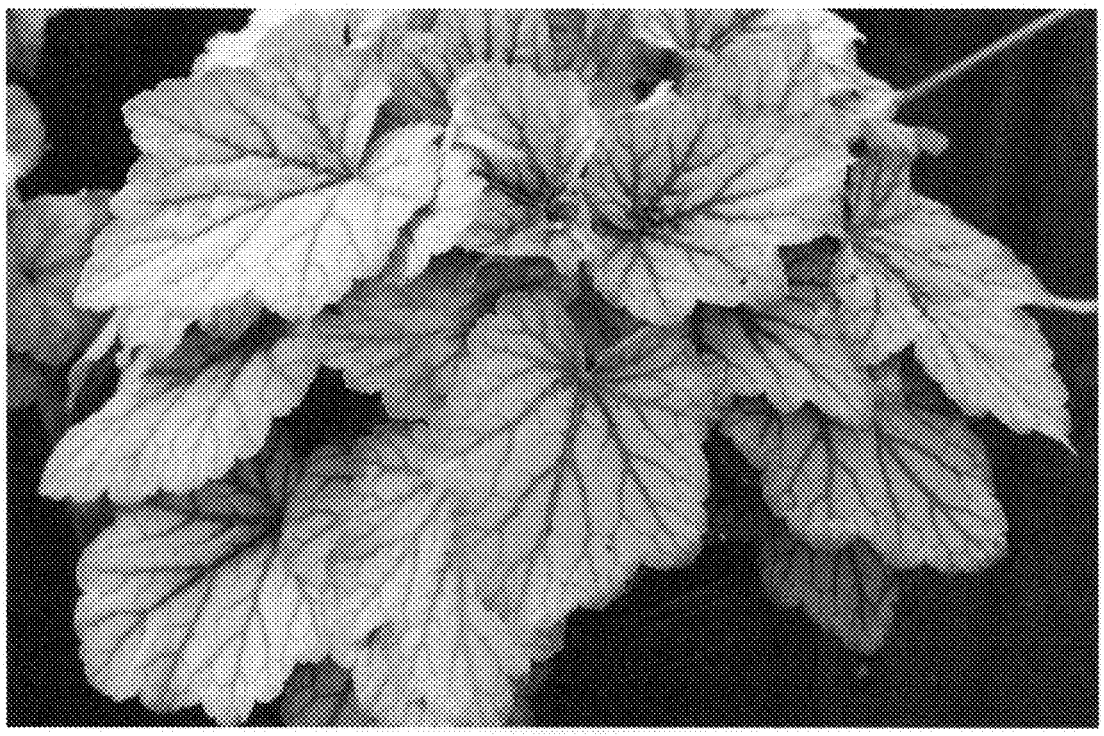

The colors in the photographs are as close as possible with the digital photography and printing techniques utilized and the color codes in the detailed botanical description accurately describe the new ×*Heucherella*.

DETAILED BOTANICAL DESCRIPTION OF THE PLANT

The following is a detailed description of one year-old plants of the new cultivar as grown indoors in one-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant habit.*—Compact, clump-forming herbaceous perennial, mounded foliage.

*Height and spread.*—Reaches about a height of about 15 cm in height (30 cm in bloom) and about 20 cm in width in a one-gallon container.

*Blooming period.*—About 8 weeks in early spring.

*Hardiness.*—At least in U.S.D.A. Zones 5 to 9.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

Propagation and growth:

*Propagation.*—In vitro propagation is the preferred method.

*Root development.*—Fully develops from a micropopagule in a 72-cell in 6 weeks in summer and 8 weeks in winter.

*Growth rate.*—Moderate to vigorous.

Foliage description:

*Leaf shape.*—Ovate.

*Leaf division.*—Simple.

*Leaf base.*—Auriculate.

*Leaf apex.*—Acute.

*Leaf venation.*—Primary palmate, secondary net-veined, conspicuous, N186A to 187B in color on upper surface and 194A and N137D in color on lower surface.

*Leaf margins.*—Lobed with 3 to 7 lobes per leaf, lobe margins crenate with abruptly acute tips.

*Leaf attachment.*—Petiolate.

*Leaf arrangement.*—Basal rosettes.

*Leaf orientation.*—Held horizontal to petiole, slightly ruffled.

*Leaf surface.*—Upper surface pubescent with 0.5 mm stiff hairs, lower surface glabrous with pubescent veins.

*Leaf color.*—Upper surface emerging; N186A, upper surface mature; 138B with 2 to 3 mm margins 138A and veins N186A to 187B, lower surface emerging and maturing; 194A.

*Leaf size.*—An average of 8 cm in length and 6.5 cm in width when mature.

*Leaf quantity.*—About 40 per one-liter container.

*Petioles.*—Round in shape, an average of 4 cm in length and 3 mm in diameter, 194A in color with a base tinged N77C, surface is densely pubescent.

Flower description:

*Inflorescence type.*—Numerous minute actinomorphic flowers arranged on a branched panicle on flower scapes emerging from the base of the rosette.

*Inflorescence size.*—Reaches an average of 20 cm in height and 5 cm in width in full bloom.

*Flower fragrance.*—None.

*Flower quantity.*—Average of 60 flowers per inflorescence.

*Flower lastingness.*—Average of 5 days per flower, individual panicles bloom for about 3 weeks, flowers self cleaning.

*Flower buds.*—Globose to obovate, average of 2 mm in diameter and 2 mm in depth, 144B in color.

*Flower aspect.*—Held slightly downward on pedicels held at 45° angle from peduncle.

*Flower shape.*—Campanulate, with base implanted in hypanthium where sepals, petals and filaments are fused.

*Flower size.*—Average of 5 mm in length and 4 mm in diameter.

*Petals.*—About 5, narrowly elliptic in shape and emerge from between sepals in hypanthium, margin is entire, apex is abruptly acuminate, about 3 mm in length and 1 mm in width, upper and lower surface is glabrous, color of upper and lower surface when opening and fully opened is NN155C, color of both surfaces fades to N155D.

*Calyx.*—Campanulate, sepals fused at base to 1 mm hypanthium, 5 mm in diameter and 4 mm in depth.

*Sepals.*—5, un-fused portion broadly oblong in shape, average of 3 mm in length and 2 mm in width, margin is entire, apex is broadly acute, base is fused, surface densely villose, color of upper surface; 145A at apex and 145D at base, color of lower surface; 138C at apex and 193C at base.

*Rachis* (*flower scape*).—Average of 30 cm in length and 6 mm in width, 144B in color, pubescent surface, held at about 20° from vertical.

*Peduncles.*—Round in shape, an average of 1 cm in length and 1 mm round, densely pubescent, 144B in color and becoming 71A towards base.

*Pedicels.*—Average of 1.3 cm in length and 1 mm round, densely pubescent, 144B in color, held at 20° to peduncle.

*Gynoecium.*—2 Pistils, club-shaped, about 5 mm in length, stigmas are minute and 155C in color, styles are continuous with ovary, about 4 mm in length and 155C in color, ovary is superior and 155C in color.

*Androecium.*—Average of 5 stamens, if present (sometimes vestigial), anthers are ovate in shape, basifixed, about 0.2 mm in length and 155B in color, filaments are 5 mm in length and 155C in color, no pollen was detected.

*Seed.*—Seed development of the new cultivar has not been observed.

It is claimed:

1. A new and distinct cultivar of ×*Heucherella* plant named 'Blue Ridge' as herein illustrated and described.

* * * * *